(12) United States Patent
Pfaff

(10) Patent No.: US 8,831,888 B2
(45) Date of Patent: Sep. 9, 2014

(54) METHOD OF PROCESSING SPECTROMETRIC DATA

(75) Inventor: Hans Pfaff, Bremen (DE)

(73) Assignee: Thermo Fisher Scientific (Bremen) GmbH, Bremen (DE)

( * ) Notice: Subject to any disclaimer, the term of this patent is extended or adjusted under 35 U.S.C. 154(b) by 505 days.

(21) Appl. No.: 12/472,262

(22) Filed: May 26, 2009

(65) Prior Publication Data

US 2009/0299653 A1 Dec. 3, 2009

(30) Foreign Application Priority Data

May 30, 2008 (EP) ..................... 08251890

(51) Int. Cl.
*G01N 33/48* (2006.01)
*G01N 33/50* (2006.01)
*G01N 31/00* (2006.01)
*G06F 19/12* (2011.01)
*G06F 17/10* (2006.01)
*G06F 17/11* (2006.01)

(52) U.S. Cl.
CPC ............... *G06F 19/12* (2013.01); *G06F 17/10* (2013.01); *G06F 17/11* (2013.01)
USPC .................................. 702/19; 702/22; 702/27

(58) Field of Classification Search
None
See application file for complete search history.

(56) References Cited

U.S. PATENT DOCUMENTS

| | | | |
|---|---|---|---|
| 5,245,186 A * | 9/1993 | Chait et al. ..................... | 250/288 |
| 5,946,117 A * | 8/1999 | Meli et al. ........................ | 398/80 |
| 6,873,915 B2 * | 3/2005 | Hastings .......................... | 702/22 |
| 2005/0059017 A1 * | 3/2005 | Oldham et al. ................... | 435/6 |

FOREIGN PATENT DOCUMENTS

WO    WO 2006/002537 A1 *   1/2006

OTHER PUBLICATIONS

Senko et al. Determination of monoisotopic masses and ion populations for large biomolecules from resolved isotopic distributions. Journal of the American Society of Mass Spectrometry, 1995, vol. 6, pp. 229-233.*
Skoog et al. Fundamentals of Analytical Chemistry, Sixth Edition. New York: Saunders College Publishing, 1992, pp. 6-7 and 22-23.*
Janssens et al. Evaluation of three zero-area digital filters for peak recognition and interference detection in automated spectral data analysis. Analytical Chemistry, vol. 63, 1991, pp. 320-331.*

Eng et al., "An Approach to Correlate Tandem Mass Spectral Data of Peptides with Amino Acid Sequences in a Protein Database," J Am Soc Mass Spectrom, 1994 (5), pp. 976-989.
S. E. Stein, "An Integrated Method for Spectrum Extraction and Compound Identification from Gas Chromatography/Mass Spectrometry Data," J Am Soc Mass Spectrom, 1999 (10), pp. 770-781.
Lam et al., "Development and validation of a spectral library searching method for peptide identification from MS/MS," Proteomics, 2007 (7), pp. 655-667.
Kaltenbach et al., "SAMPI: Protein Identification with Mass Spectra Alignments," BMC Bioinformatics 2007, 8:102.
Zheng et al., "2D NMR metabonomic analysis: a novel method for automated peak alignment," Bioinformatics 2007, vol. 23 (21), pp. 2926-2933.
Sebastian Boecker et al., "Decomposing Metabolomic Isotope Patterns," Algorithms in Bioinformatics Lecture Notes in Computer Science, XP019042831, vol. 4175, pp. 12-23, (2006).
D. Goldberg et al., "Automatic Annotation of Matrix-Assisted Laser Desorption/Ionization N-Glycan Spectra," Proteomics, XP002518995, vol. 5, No. 4, (2005), pp. 865-875.
J. Zhang et al., "Predicting Molecular Formulas of Fragment Ions with Isotope Patterns in Tandem Mass Spectra," EEE/ACM Transactions on Computational Biology and Bioinformatics, XP002518996, vol. 2, No. 3, (2005) , pp. 217-230.
A. Tenhosaari, "Computer-Assisted Composition Analysis of Unknown Compounds by Simultaneous Analysis of the Intensity Ratios of Isotope Patterns of the Molecular Ion and Daughter Ions in Low-Resolution Mass Spectra," Organic Mass Spectrometry, XP002518998, vol. 23, No. 4, (1988), pp. 236-239.
N. Zhang et al., "ProbID: A Probabilistic Algorithm to Identify Peptides through Sequence Database Searching Using Tandem Mass Spectral Data," Proteomics, XP002518997, vol. 2, No. 10 (2002), pp. 1406-1410.
M. Gentzel et al., "Preprocessing of Tandem Mass Spectrometric Data to Support Automatic Protein Identification," Proteomics, XP002494128, vol. 3, (2003), pp. 1597-1610.

* cited by examiner

*Primary Examiner* — Russell S Negin
(74) *Attorney, Agent, or Firm* — Charles B. Katz; Timothy J. Ohara

(57) ABSTRACT

A method of characterizing a sample from spectrometric data using calculation of spectral distance values is disclosed, for use in the field of mass spectrometry. Molecular formula assignment of peaks in mass spectral data is difficult and time-consuming, and the invention provides a computer implemented method of finding a most likely elemental composition of a measured spectral peak of interest. The method analyzes isotopic peaks in a portion of the spectrum, using both their mass positions and intensities, to determine a spectral distance between those peaks and isotopic peaks of a candidate composition, finding peaks that match (140). A pattern spectral distance is determined (150) to provide a measure of the correspondence between a set of those peaks in the measured spectrum and peaks of each of a number of candidate compositions. The spectral fit is used to determine a most likely candidate composition.

13 Claims, 2 Drawing Sheets a peak whose position lies within a predetermined tolerance of the position of the said measured peak of interest;
(b) forming a set of candidate compositions from the identified plurality of elemental compositions;
(c) generating a theoretical isotopic spectrum for each of the candidate compositions in the said formed set thereof,
(d) selecting peaks within each theoretical isotopic spectrum thus generated, for further processing;
(e) for each candidate composition of the set, in turn:
  (i) scaling the intensity of at least one of: all the selected peaks of the theoretical isotopic spectrum of the particular candidate composition under consideration, and/or all the peaks of the measured mass spectrum, to reduce the difference between the intensities of the peak of interest and the corresponding peak of the candidate composition;
  (ii) calculating a spectral distance, SD, between peaks in the theoretical isotopic spectrum and peaks in the measured spectrum based upon both the difference dM in the relative positions of a given peak in the theoretical isotopic spectrum and a given peak in the measured spectrum, and also the relative differences dI in scaled intensity thereof, wherein SD increases monotonically with dM and dI;
  (iii) either:
    for the peaks in the theoretical isotopic spectrum selected in step (d), identifying the peak in the measured spectrum which is considered most closely to correspond with a particular one of the peaks in the theoretical isotopic spectrum by determining which of the measured peaks has the lowest SD; or
    for the peaks in the measured spectrum, identifying the peak in the theoretical isotopic spectrum selected in step (d) which is considered most closely to correspond with a particular one of the peaks in the measured spectrum by determining which of the theoretical isotopic peaks has the lowest SD;
  (iv) calculating a pattern spectral distance (PSD) for a particular candidate composition, based upon a combination of both dM and dI between the measured peaks and the theoretical isotopic peaks, where the measured or theoretical isotopic peaks are those which have been identified in step (e) (iii), and wherein PSD increases monotonically with dM and dI;
  (v) normalizing the PSD for n, the number of selected peaks in the theoretical isotopic spectrum;
(f) identifying which of the set of candidate elemental compositions of the measured peak of interest is the most likely elemental composition thereof, by determining which candidate composition has the lowest PSD; and
(g) outputting data representative of the identified most likely elemental composition of the measured peak of interest.

Calculating the spectral distance, SD, which enables corresponding peaks to be identified, involves a measure of both the position difference dM and the intensity difference dI between theoretical isotopic peaks and the measured peaks. Different functions may be used to represent SD, provided SD increases monotonically with dM and dI. The SD is described in more detail below. In preferred embodiments, SD is defined as any of:

METHOD OF PROCESSING SPECTROMETRIC DATA

FIELD OF THE INVENTION

This invention relates to a method of processing spectrometric data. The method is preferably though not of necessity implemented in computer software, for analysis of mass spectrometric data.

BACKGROUND TO THE INVENTION

Ultra-high resolution mass spectrometry, such as is achievable using a Fourier transform ion cyclotron resonance mass spectrometer (FT-ICR-MS), or an Orbitrap™ mass spectrometer, enables the identification of thousands of different molecular formulas in organic matter. Coupled with liquid chromatography (LC), accurate mass determination of components of complex mixtures can be made on a routine basis. Applications include, amongst others, screening combinatorial chemistry libraries and identifying metabolites related to drug discovery, screening for anabolic steroids in illegal cocktails and fungal metabolites in culture extracts, and elucidating unknown compounds in environmental water.

The output from the mass spectrometer must be interpreted before samples can be characterised, and this presents technical problems. Molecular formula assignment from mass data is most critical and time-consuming. Accurate mass measurement by mass spectrometry is a common technique to determine elemental composition, facilitated by ultra high resolution mass spectrometers. Despite technological advances and improved mass accuracy, often the mass accuracy alone does not provide unequivocal identification. In many cases, several different structural formulae can be identified for the same molecular mass. The number of candidate formulae increases exponentially with mass, making high mass molecular determination particularly challenging. Therefore, automated procedures are required for an efficient exploitation of the extensive data sets produced by mass spectrometry, when characterising samples.

Various methods of determining the elemental composition of molecular mass peaks have been proposed, yet there remains a need for a method that produces results of higher specificity and accuracy. Other workers have reported the use of the accurate mass of measured peaks together with the relative isotopic abundances in order to identify the elemental composition of molecular peaks measured by high resolution mass spectrometry, see for example Breitling, R.: Pitt, A. R. & Barrett, M. P. "Precision mapping of the metabolome", *Trends in Biotechnology*, 2006, 24, 543-548; Boecker, S.; Letzel, M.; Liptak, Z. & Pervukhin, A. "Decomposing Metabolomic Isotope Patterns", *Algorithms in Bioinformatics*, 2006, 12-23; and, Grange, A. H.; Winnik, W.; Ferguson, P. L. & Sovocool, G. W. "Using a triple-quadrupole mass spectrometer in accurate mass mode and an ion correlation program to identify compounds", *Rapid Communications in Mass Spectrometry*, 2005, 19, 2699-2715.

SUMMARY OF INVENTION

According to the present invention there is provided a computer implemented method of characterizing a sample by identifying a most likely elemental composition of a measured peak of interest in a spectrum obtained from that sample, comprising the steps of:
(a) identifying, for the peak of interest in the spectrum of the sample, a plurality of elemental compositions having $$SD=\sqrt{((dM/M_{exp})^2+(dI/I_{exp})^2)} \quad (a)$$

$$SD=|dM/M_{exp}|+|dI/I_{exp}| \quad (b)$$

$$SD=\sqrt{((dM/M_{exp})^2)+dI/I_{exp}|} \quad (c)$$

$$SD=|dM/M_{exp}|+\sqrt{((dI/I_{exp})^2)} \quad (d)$$

wherein
$M_{exp}$=expected positional error,
$I_{exp}$=expected intensity error.

The pattern spectral distance, PSD, is based upon dM and dI, the position and intensity differences between each theoretical isotopic peak, ip, in the theoretical spectrum for a given candidate composition and the corresponding peak in the measured spectrum. Different functions may be used to represent PSD, provided PSD increases monotonically with dM and dI. The PSD is described in more detail below. Preferably, PSD is defined as any of:

$$PSD=\sqrt{(\Sigma(dM_{ip}/M_{exp})^2+\Sigma(dI_{ip}/I_{exp})^2)} \quad (a)$$

$$PSD=\Sigma|dM_{ip}/M_{exp}|+\Sigma|dI_{ip}/I_{exp}| \quad (b)$$

$$PSD=\sqrt{(\Sigma(dM_{ip}/M_{exp})^2)+\Sigma|dI_{ip}/I_{exp}|} \quad (c)$$

$$PSD=\Sigma|dM_{ip}/M_{exp}|+\sqrt{(\Sigma(dI_{ip}/I_{exp})^2)} \quad (d)$$

wherein
$\Sigma$ is the sum over all selected theoretical isotopic peaks and their corresponding measured peaks,
$dM_{ip}$ is the positional difference between the identified corresponding measured peak and selected theoretical isotopic peak, and
$dI_{ip}$ is the intensity difference between the identified corresponding measured peak and selected theoretical isotopic peak.

Various criteria may be used for selecting theoretical isotopic peaks for further processing. A preferred criterion for selecting a theoretical isotopic peak comprises applying a threshold, such that only peaks of the theoretical isotopic spectrum having intensities greater than the threshold are selected for further processing. Preferably, the threshold is mathematically related to the noise in the measured spectrum. More preferably, the threshold in percent is set to $100 \cdot (4 \cdot I_{noise}/B)$, where B is the intensity of the identified peak of interest and the measured noise value of this peak is $I_{noise}$.

In preferred embodiments, between steps (e)(iii) and (e)(iv) the selected theoretical isotopic peaks and/or the peaks of the measured spectrum are scaled in intensity so as to minimize the sum of the difference in intensities, dI, between the intensity of each selected theoretical isotopic peak and the intensity of the corresponding measured peak. Preferably, such scaling is performed using a scaling factor N which is calculated and applied according to:

$$I_r = N \cdot I_1$$

where:
$I_r$ are the scaled peak intensities, and
$I_1$ are the intensities of the peaks in the spectrum to be scaled, either the selected theoretical isotopic peak intensities or the measured peak intensities;
and where:
$I_{(1,abs)}$ is the absolute intensity of the peak in the spectrum to be scaled,
$I_{(2,abs)}$ is the absolute intensity of the corresponding peak in the other spectrum which is not to be scaled, and all summations are over all the peaks in the spectrum to be scaled;

and in which the scaling factor is calculated as one of $$N=\Sigma I_{(2,abs)}/\Sigma I_{(1,abs)} \quad (a)$$

$$N=\Sigma(I_{(2,abs)} \cdot I_{(1,abs)})/\Sigma(I_{(1,abs)} \cdot I_{(1,abs)}) \quad (b)$$

Preferably, the step of normalizing the PSD for n comprises multiplying the PSD by $1/\sqrt{(2*n)}$.

Another preferred feature of the invention comprise weighting the PSD according to the abundance of the peaks in either the theoretical isotopic mass spectrum or the measured mass spectrum such that a mass and/or intensity error of a less intense peak affects the PSD less than the same mass or intensity error of a more intense peak. In such cases, preferably the weighted PSD is calculated according to one of:

$$PSD=\sqrt{[((dM_1/M_{exp})^2*I_{1f})+((dM_2/M_{exp})^2*I_{2f})+\ldots+((dI_1/I_{exp})^2*I_{1f})+((dI_2/I_{exp})^2*I_{2f})+\ldots]} \quad (a)$$

$$PSD=\sqrt{[((dM_1/M_{exp})+((dM_2/M_{exp})+\ldots+((dI_1/I_{exp})^2*I_{1f})+((dI_2/I_{exp})^2*I_{2f})+\ldots]} \quad (b)$$

$$PSD=\sqrt{[((dM_1/M_{exp})^2*I_{1f})+((dM_2/M_{exp})^2*I_{2f})+\ldots+((dI_1/I_{exp})^2)+((dI_2/I_{exp})^2)+\ldots]} \quad (c)$$

and where:
the intensity of the selected theoretical isotopic mass peak is $I_{ip}$; and
$I_{1f}$, $I_{2f}$ etc. are fractional intensities.

More preferably in cases (a), (b) or (c) above for weighting the PSD, the step of normalizing the PSD for n, the number of peaks in the theoretical isotopic spectrum, comprises multiplying the PSD by $$1/\sqrt{[2*I_{1f}+2*I_{2f}+\ldots]} \quad (a)$$

$$1/\sqrt{[n+I_{1f}+I_{2f}+\ldots]} \quad (b)$$

$$1/\sqrt{[n+I_{1f}+I_{2f}+\ldots]} \quad (c)$$

for the cases (a), (b) and (c) respectively.

In a preferred feature of the method, a peak may be defined as missing if SD is larger than or equal to a given threshold, and that the calculation of the PSD involves applying a penalty for such missing peaks, the penalty further increasing the value of PSD. A preferred threshold is 1.0. The penalty applied is preferably calculated based on the signal to noise ratio, S/N, the peak would be expected to have, had it existed in the measured spectrum. preferably, the penalty is dE, and dE is applied in one of the following ways:
(a) if $dM_{ip}>M_{exp}$ the term $dM_{ip}/M_{exp}$ is replaced with dE
(b) if $dI_{ip}>I_{exp}$ the term $dI_{ip}/I_{exp}$ is replaced with dE
(c) if both $dM_{ip}>M_{exp}$ and $dI_{ip}>I_{exp}$ both the term $dM_{ip}/M_{exp}$ and $dI_{ip}/I_{exp}$ are replaced with dE,
and where dE is greater than or equal to 1.0.

Preferably, the positions of the measured peaks and/or the positions of the theoretical isotopic peaks are indicative of and related to quantities indicative of physical mass of ions/compounds/materials/molecules. The quantity indicative of physical mass is preferably one or a combination of any two or more of: time of flight, frequency, voltage, magnetic field, angular deflection.

In a further aspect, the present invention provides a computer program having elements of program code which, when executed, carry out the method of any preceding claim. In another aspect, the present invention provides a computer readable medium when carrying said program.

Thus, in accordance with the present invention, scaled or normalized (these terms may be interchanged herein) quantities associated with the position (e.g. the mass or a quantity related thereto) and the intensity of measured peaks are employed to substantially improve the correct assignment of elemental compositions to measured molecular peaks. The time thus taken to characterize a given sample is thereby greatly reduced, and the accuracy of that sample characterization, is improved.

DETAILED DESCRIPTION

Figure 1:
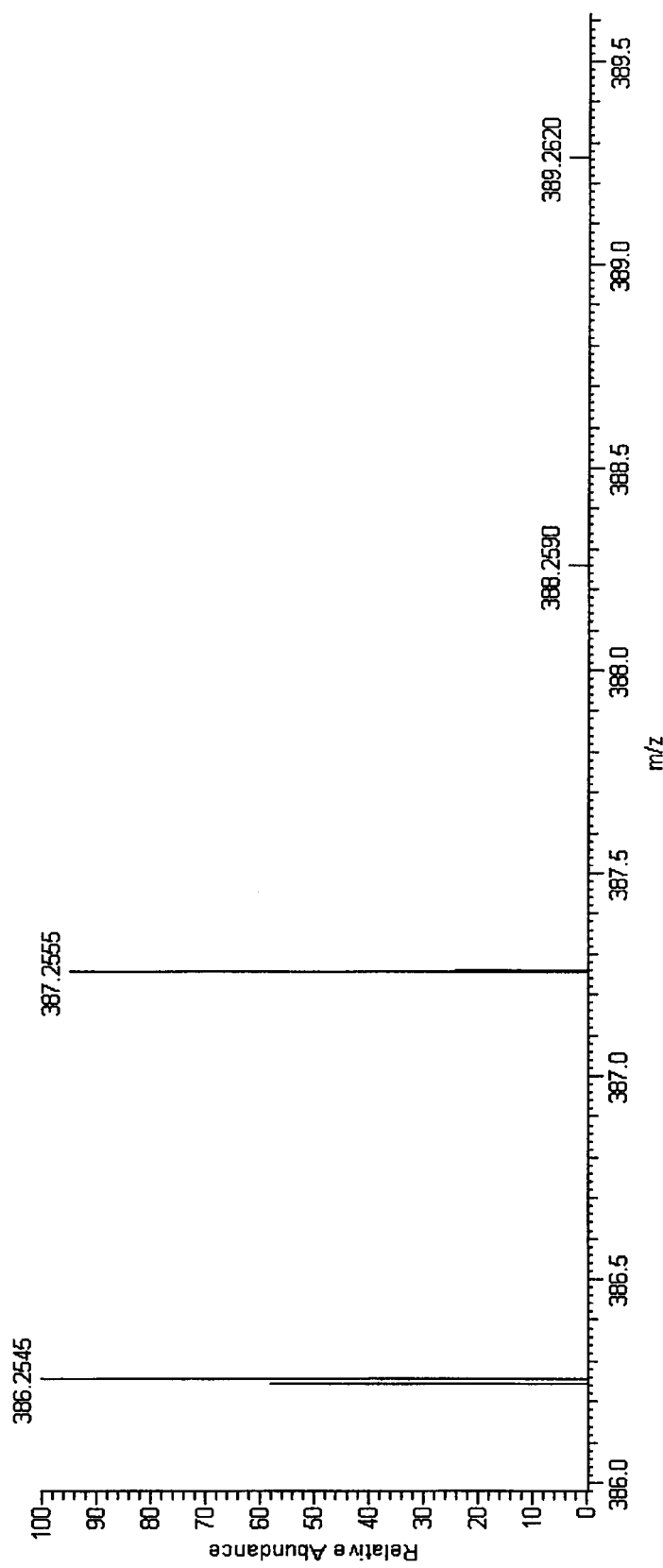
FIG. 1 shows a mass spectrum of the compound Buspirone obtained from a liquid chromatography (LC) instrument coupled to a mass spectrometer (MS)

The invention will now be described in more detail with reference to the mass spectrum of a known compound, Buspirone. However, it will be appreciated that the individual features of the invention described are of general applicability. FIG. 1 shows a mass spectrum of Buspirone, obtained by liquid chromatography mass spectrometry (LC-MS). The mass analysis was carried out using an FT-ICR mass spectrometer operated at high resolution. Specific details of the experimental arrangement (i.e. the specific components employed in the mass spectrometer arrangement) are not critical to an understanding of the present invention and, in any event, various embodiments would be familiar to the skilled reader. Such arrangements are shown, just as examples, in U.S. Pat. No. 6,987,261 and U.S. Pat. No. 7,211,794 and in Parts per Million Mass Accuracy on an Orbitrap Mass Spectrometer via Lock Mass Injection into a C-trap", Mol. Cell. Proteomics, December 2005; 4: 2010-2021; Jesper V. Olsen, Lyris M. F. de Godoy, Guoqing Li, Boris Macek, Peter Mortensen, Reinhold Pesch, Alexander Makarov, Oliver Lange, Stevan Horning, and Matthias Mann. No further details of the mass spectrometric arrangement are accordingly provided.

The monoisotopic mass of the MH+ form of Buspirone is known to be 386.255052 Daltons. (The monoisotopic mass is the mass of the molecule when that molecule is composed of the most naturally abundant isotopes of the elements it comprises.) This mass spectrum of a sample is typical, and is used here as a test to explain the method embodying the present invention. The major peak has a measured mass of 386.2545. Preferably, the measured mass peak for which the most likely elemental composition is to be identified is the monoisotopic mass peak in the measured spectrum.

A prior art elemental composition calculation routine is employed to obtain a list of elemental composition candidates that could match the measured molecular peak to within 5 ppm in mass. This elemental composition calculation routine is widely used by workers in the field. An example can be found at http://library.med.utah.edu/masspec/elcomp.htm. The routine requires a list of elements to use, with minimum and maximum numbers of each that may be combined together. A mass tolerance is also required, together with the exact mass. Filters can also be applied, such as the number of ring and double bond equivalents (RDB) or the electron rule (even, odd or none), as is well known by the skilled person. The routine then starts with the minimum number of all the elements in the list and increments the number of atoms of each element in turn, to find all possible permutations of elements that match the exact mass within the mass tolerance. It then checks any filters and if the filter is passed, the composition is returned as an elemental composition candidate for the molecule.

For this test, it is assumed that little is known about the nature of the compound, and the following elements are considered possible components, with their respective atomic quantities: Carbon (0 to 200), Hydrogen (0 to 400), Oxygen (0 to 20), Nitrogen (0 to 20), Sulfur (0 to 5), Chlorine (0 to 3) and Fluorine (0 to 3).

The list of candidates produced by one such above described prior art elemental composition calculation process is shown in Table 1, together with the mass deviation of each candidate from that of the measured monoisotopic mass.

TABLE 1

Candidates for the monoisotopic mass 386.2545 Daltons found by the prior art elemental composition calculation technique.

| | Elemental composition candidate | Mass deviation [ppm] |
|---|---|---|
| 1 | C18•H36•N3•[35]Cl1•F3. | 0.163 |
| 2 | C21•H40•O1•N1•[32]S2. | −0.214 |
| 3 | C13•H36•O4•N7•[32]S1. | 0.259 |
| 4 | C23•H37•[35]Cl1•F2. | −0.354 |
| 5 | C11•H30•O2•N11•F2. | −0.394 |
| 6 | C4•H26•O2•N20. | 0.747 |
| 7 | C16•H33•N9•[35]Cl1. | 0.786 |
| 8 | C16•H31•O2•N8•F1. | −0.911 |
| 9 | C17•H37•O7•N1•F1. | −0.925 |
| 10 | C11•H32•N12•[35]Cl1•F1. | 1.304 |
| 11 | C21•H33•O1•N2•F3. | 1.424 |
| 12 | C21•H32•O2•N5. | −1.428 |
| 13 | C20•H36•O6•N1. | 2.034 |
| 14 | C19•H30•O1•N8. | 2.048 |
| 15 | C13•H34•O1•N9•[35]Cl1•F1. | −2.172 |
| 16 | C15•H35•O6•N4•F1. | 2.552 |
| 17 | C14•H29•O1•N11•F1. | 2.565 |
| 18 | C18•H38•O3•N1•F2•[32]S1. | 2.595 |
| 19 | C9•H31•N14•F1•[32]S1. | −2.686 |
| 20 | C18•H35•O1•N6•[35]Cl1. | −2.69 |
| 21 | C6•H28•O3•N17. | −2.729 |
| 22 | C9•H28•O1•N14•F2. | 3.082 |
| 23 | C14•H32•N11•[32]S1. | −3.203 |
| 24 | C19•H38•N4•[32]S2. | 3.262 |
| 25 | C20•H38•O1•[35]Cl1•F3. | −3.313 |
| 26 | C11•H34•O3•N10•[32]S1. | 3.736 |
| 27 | C14•H37•N7•F1•[32]S2. | 3.779 |
| 28 | C16•H35•N5•F3•[32]S1. | −3.826 |
| 29 | C13•H32•O3•N8•F2. | −3.87 |
| 30 | C15•H38•N7•[35]Cl2. | −3.951 |
| 31 | C15•H37•O4•N5•[35]Cl1. | 4.249 |
| 32 | C21•H36•N2•F2•[32]S1. | −4.344 |
| 33 | C24•H32•N2•F2. | 4.383 |
| 34 | C18•H33•O3•N5•F1. | −4.387 |
| 35 | C19•H31•N5•F3. | 4.901 |
| 36 | C23•H34•O3•N2. | −4.905 |

There are some 36 candidates, even for this relatively light (less than 400 Daltons) monoisotopic mass, and even employing a relatively strict mass tolerance of 5 ppm. Because the mass deviations are spread fairly uniformly, it is not possible to be confident which the correct composition is.

The experienced mass spectroscopist faced with these results would now apply additional knowledge to try and reduce the number of possible candidates. For example, if it was known that the compound contains sulfur and/or chlorine, it would be possible to exclude some candidate compositions. For example, the presence of chlorine changes the isotope pattern of the compound significantly. Information is present in the isotopic pattern which the mass spectroscopist uses to narrow down the candidate list, but this is done manually, requires skill and experience, and is very time consuming. Embodiments of the present invention use a method which can be automated and, as will be shown, reduce the candidate list typically to just one candidate having a very high probability of being the correct composition.

A method embodying the present invention will now be described in a simplest form. Briefly, the method uses both the positions of the peaks on the mass scale, and the intensities of the peaks, and then looks at the peaks expected in the spectrum from the possible isotopes of the elements of the candidate compositions.

Figure 2:
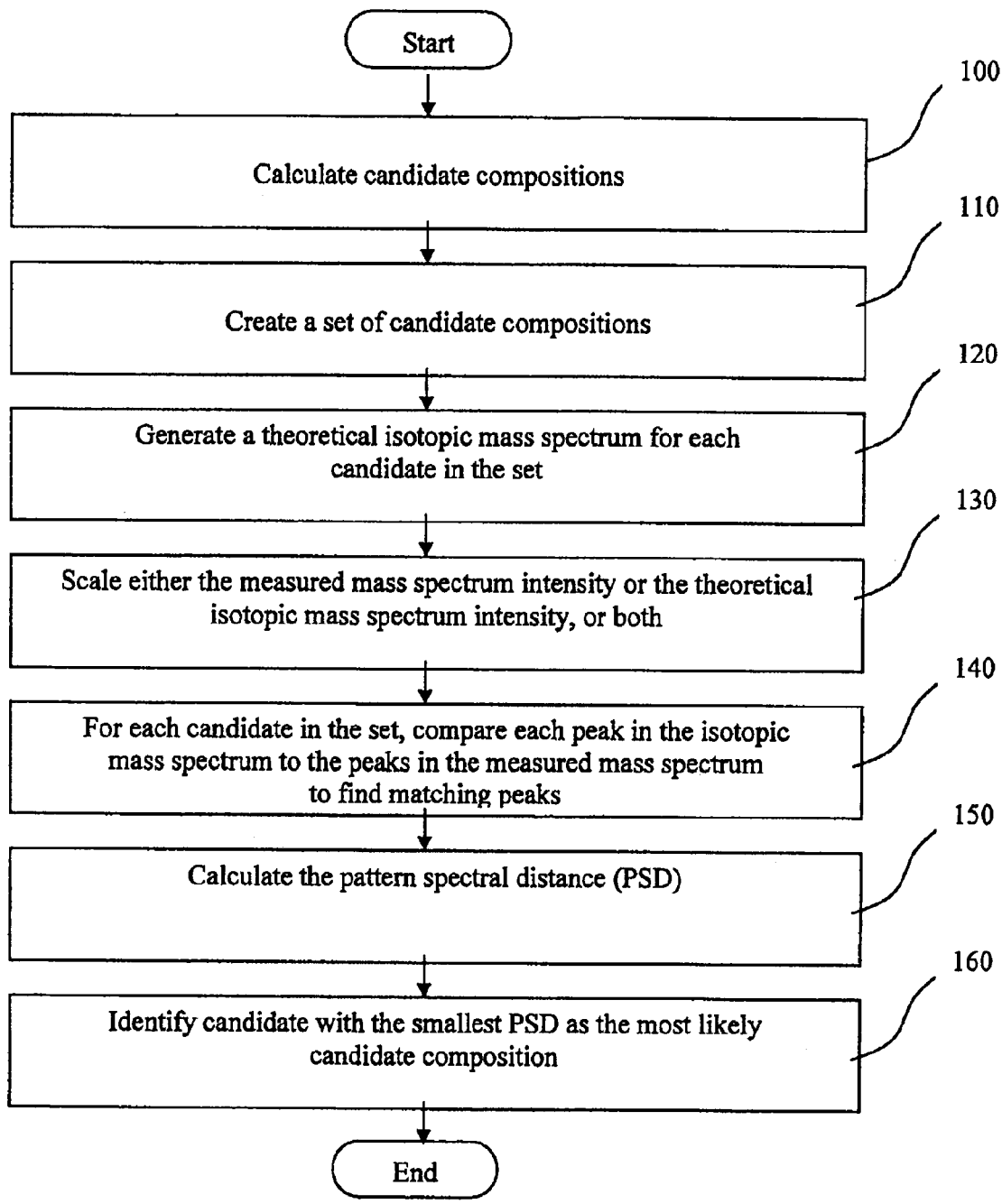
FIG. 2 shows a flow chart illustrating the main steps of a method in accordance with a preferred embodiment of the invention.

FIG. 2 shows a flow chart outlining in more detail the steps of the method that illustrate an embodiment of the present invention.

First, at step 100, the candidate compositions are calculated as in the prior art elemental composition calculation method. A set of candidate compositions is then created at step 110, which might be all the compositions produced by the elemental composition calculation, or might be a selected portion (subset) of them. Next at step 120, each candidate composition in the set in turn is considered, and the possible isotopic variants are calculated, giving a theoretical isotopic mass spectrum for each candidate in the set. This spectrum has peaks at each point on the mass scale that would be expected from each combination of the isotopes of each element in the composition. These mass peaks have intensities in accordance either with the natural abundances of the isotopes, or if the sample has been isotopically enriched, perhaps to label it, the enriched intensities are used. These spectra are then compared with the portion of the measured mass spectrum of interest, in turn for each candidate composition.

For each theoretical isotopic mass spectrum, each peak in that spectrum is compared at step 140 with those peaks in the measured mass spectrum unless the peak in the theoretical isotopic mass spectrum is very small, in which case only peaks above a threshold are selected. Each selected peak of the theoretical isotopic mass spectrum is compared in turn with the peaks in the measured mass spectrum. To carry out this comparison, a precursor normalization step (130) is first carried out. Specifically, the portion of the measured mass spectrum (the window about the monoisotopic mass peak) containing the isotope pattern of interest is firstly scaled or normalized so that the monoisotopic mass peak in the measured spectrum has substantially the same intensity, preferably exactly the same intensity, as the monoisotopic peak in the theoretical isotopic mass spectrum. The preferred technique for normalization of the mass will be described in further detail below.

For the first scaling, either of the measured spectrum and the theoretical isotopic mass spectrum may be scaled or they may each be scaled in intensity so that the described peaks become of substantially the same intensity. In general, it should be appreciated that it may not be necessary to make the intensities substantially the same but rather it may be sufficient to apply a first scaling to the measured mass spectrum intensity and/or the theoretical isotopic mass spectrum intensity to reduce the difference in the peak intensity of the measured peak and the peak intensity of the corresponding peak in the theoretical isotopic mass spectrum. The first scaling is preferably performed after the theoretical isotopic spectra have been generated, however it is possible that the first scaling may form part of the step of generating the theoretical isotopic mass spectra by providing that the theoretical isotopic mass spectra are generated so as to have a minimised difference, as previously explained, in the peak intensity of the measured peak and the peak intensity of the corresponding peak in the theoretical isotopic mass spectrum.

The peaks in the theoretical isotopic mass spectrum are then compared with the relevant peaks in the measured mass spectrum, to identify which peaks are present at the corresponding positions on the mass scale, and which have the closest match to the expected intensity, as will be described further below. The method of this step uses both the mass position and intensity of the peaks in this process, and a quantity termed the 'spectral distance' (SD) is calculated, based upon one of a variety of possible mathematical combinations of peak position and intensity differences (dM and dI), and the peak in the measured mass spectrum representing a 'best match' to a given theoretical isotopic mass peak under consideration is identified on the basis of a minimum SD.

Optionally, if the measured mass spectrum does not contain the expected peak within a given mass or intensity window, a penalty is applied. Optionally, as noted above, if the theoretical peak is of low intensity compared to the baseline noise of the measured mass spectrum, that theoretical peak is excluded from the comparison process.

A quantity termed the pattern spectral distance, PSD, is then calculated at step 150. The pattern spectral distance is a measure of the correspondence between the peaks of the isotopic spectrum for the composition candidate, and those of the measured mass spectrum. This pattern spectral distance will be further explained below.

Optionally, to better express to the user the degree of correspondence between the candidate composition and the measured spectrum, the PSD is converted to a pattern spectral fit, PSF, ranging from 0 to 100%.

This method is performed for each composition candidate of the set. The candidate having the smallest pattern spectral distance (and hence the highest pattern spectral fit), is the most likely composition that produced the measured mass spectrum (step 160 in FIG. 2). As will be shown below, the method provides a remarkably high differentiation between good pattern spectral fit and poor pattern spectral fit, typically indicating a single composition candidate as having a substantially closer fit than all others. Typically, when tested (for example using MS/MS or MS$^n$ analysis), the candidate with the best fit is indeed the correct candidate. The method has the advantages of high selectivity and high accuracy.

The calculation of the spectral distance and then the pattern spectral distance (step 150 in FIG. 2) will now be described in more detail along with further refinements.

A measure of the correspondence between selected peaks in the theoretical isotopic mass spectrum and those in the measured mass spectrum, SD, is obtained by combining terms which express the mass differences and intensity differences between the corresponding peaks. The method is as follows:

Firstly, as explained above in connection with FIG. 2, the measured mass spectrum intensity of the isotope pattern of interest in the appropriate window of the measured mass spectrum is scaled at step 130, to reduce the difference between the intensities of the peak of interest and the corresponding peak of the candidate composition, preferably to make the peak height of the mass peak substantially equal to the peak height of the (theoretical) candidate composition matched to it. This can be achieved by adjusting the intensity of the measured mass spectrum, the intensity of the theoretical isotopic mass spectrum, or both. In all these cases, the expression "normalized/scaled measured mass peak" or "normalized/scaled measured mass spectrum" is employed to indicate that this normalization or scaling process has been performed. Then:

(1) The peaks to be compared are identified. For each selected theoretical isotopic peak in the spectrum, the measured mass peak which has the smallest spectral distance, SD, is found, where:

$$SD = \sqrt{((dM/M_{exp})^2 + (dI/I_{exp})^2)} \qquad \text{equation (1).}$$

$M_{exp}$=expected mass error,
$I_{exp}$=expected intensity error,
dM is the mass difference between the measured mass peak and the selected theoretical isotopic peak, and
dI is the intensity difference between the measured mass peak and the selected theoretical isotopic peak.

This is the preferred method for identifying peaks, involving a measure of both the mass difference and the intensity difference between theoretical isotopic peaks and the measured mass peak. Alternative measures can be used, such as $SD=|dM/M_{exp}|+|dI/I_{exp}|$, for example, which also use a measure of both the mass difference and the intensity difference between theoretical isotopic peaks and the measured mass peak. Alternatively, combinations of such terms and those of equation (1) could be used, such as $SD=\sqrt{((dM/M_{exp})^2)}+|dI/I_{exp}|$, or $SD=|dM/M_{exp}|+\sqrt{((dI/I_{exp})^2)}$. Of course it will be appreciated that this step of identifying matching peaks can be performed by, for each measured mass peak, identifying the theoretical isotopic peak which has the smallest spectral distance, SD using the formulae above.

(2) Optionally, a further normalization or scaling step is applied in which the complete pattern of theoretical isotope peaks is best matched to the pattern of found measured mass peaks. This will be further described below. Then, a pattern spectral distance PSD is calculated. The PSD is a figure of merit (goodness of fit) between the theoretical isotopic spectrum for a given candidate elemental composition and the actual, measured spectrum (suitably scaled or normalized) around the measured mass peak of interest. The PSD is based upon dM and dI, the mass and intensity differences between each isotopic peak, ip, in the theoretical spectrum for a given candidate and that "found" peak in the measured mass spectrum having the smallest spectral distance, SD, to that isotopic peak. In the preferred implementation, PSD is calculated as:

$$PSD=\sqrt{(dM_{ip}/M_{exp})^2+\Sigma(dI_{ip}/I_{exp})^2} \qquad \text{equation (2)}$$

where:
$\Sigma$ is the sum over all ip,
$dM_{ip}$ is the mass difference between the found measured mass peak and the selected theoretical isotopic peak, and
$dI_{ip}$ is the intensity difference between the found measured mass peak and the selected theoretical isotopic peak.

In this calculation, as in the preferred calculation for SD, the differences between the masses and the differences between the intensities of the compared peaks are combined in quadrature after first normalizing them. They are normalized by dividing each dM by the expected mass error and each dI by the expected intensity error, making both terms dimensionless. The expected mass error should be related to the mass accuracy of the mass spectrometer that was used to take the measured mass spectrum and is either specified by the user or provided by the spectrometer itself. Typically the user would set the expected mass error to be three times the observed mass accuracy, as determined for the spectrometer at the relevant mass and under appropriate operating conditions. Likewise the expected intensity error is set by the user or provided by the spectrometer itself and should be based on the observed intensity error produced by the mass spectrometer under appropriate operating conditions.

Again, the measure used includes both the mass difference and the intensity difference between theoretical isotopic peaks and the measured mass peak. Again, alternative measures can be used, such as $PSD=\Sigma|dM_{ip}/M_{exp}|+\Sigma|dI_{ip}/I_{exp}|$, for example, or combinations of such terms and those in equation (2), such as $PSD=\sqrt{(\Sigma(dM_{ip}/M_{exp})^2)}+\Sigma|dI_{ip}/I_{exp}|$, or $PSD=\Sigma|dM_{ip}/M_{exp}|+\sqrt{(\Sigma(dI_{ip}/I_{exp})^2)}$.

Due to the nature of the calculation of PSD such as is described by equation (2), the PSD will increase in magnitude with the total number of isotopic peaks, n, in the isotopic pattern being compared. This would make an isotopic peak pattern containing many peaks have a higher PSD than a pattern containing few peaks, even if the peaks in the multiple peak pattern actually matched more closely—their individual spectral distances being smaller. To remove this effect, the PSD is itself normalized by the maximum expected PSD. The maximum PSD expected is when every peak in the isotope pattern has a mass error equal to the expected mass error, $M_{exp}$, and has an intensity error equal to the expected intensity error, $I_{exp}$. Equation (2) then reduces to:

$$PSD_{max}=\sqrt{(2 \cdot n)} \qquad \text{equation (3).}$$

This is the preferred correction, but others could be used. If the expected mass error and/or expected intensity error input by the user were mistakenly set too low, it is possible that the PSD could be greater than $PSD_{max}$. To avoid this, the PSD value is given a maximum ceiling, being the smaller of 1.0, or $PSD/PSD_{max}$.

The expected mass and intensity errors of a measured peak of high abundance are for statistical reasons expected to be lower than the mass and intensity errors of a smaller peak. A further refinement to the method is to weight the pattern spectral distance according to the abundance of the peaks in the spectrum to take account of this. This is described as abundance weighting. If this optional approach is taken, a mass and/or intensity error of a small peak affects the pattern spectral distance less than the same mass or intensity error of a large peak. The weighting can take account of one or both of these cases. If both are to be accounted for, and the intensity of the theoretical isotopic mass peak is $I_{ip}$, the calculation for PSD becomes:

$$PSD=[1/\Sigma I_{if}]\cdot\sqrt{[((dM_1/M_{exp})^2*I_{1f})+((dM_2/M_{exp})^2*I_{2f})+\ldots+((dI_1/I_{exp})^2*I_{1f})+((dI_2/I_{exp})^2*I_{2f})+\ldots]} \qquad \text{equation (4).}$$

where $I_{1f}$, $I_{2f}$ etc. are fractional intensities and $\Sigma I_{if}$ is the sum of all the fractional intensities. Where just mass errors are corrected, equation (4) reduces to $PSD=[1/\Sigma I_{if}]\cdot\sqrt{[((dM_1/M_{exp})^2*I_{1f})+((dM_2/M_{exp})^2*I_{2f})+\ldots+((dI_1/I_{exp})^2)+((dI_2/I_{exp})^2)+\ldots]}$. Where just intensity errors are corrected, equation (4) reduces to $PSD=[1/\Sigma I_{if}]\cdot\sqrt{[((dM_1/M_{exp})+((dM_2/M_{exp})+\ldots+((dI_1/I_{exp})^2*I_{1f})+((dI_2/I_{exp})^2*I_{2f})+\ldots]}$ Likewise the correction is applied to the calculation of $PSD_{max}$. Now the mass error is equal to the expected mass error, and the intensity error is equal to the expected intensity error, so the equation reduces to:

$$PSD_{max}=[1/\Sigma I_{if}]\cdot\sqrt{[2*I_{1f}+2*I_{2f}+\ldots]} \qquad \text{equation (5).}$$

Equation (5) applies to the case where both the mass and intensity errors are being corrected. In the case where just one of the mass or intensity is corrected, equation (5) reduces to $[1/\Sigma I_{if}]*\sqrt{[n+I_{1f}+I_{2f}+\ldots]}$.

The normalized and abundance weighted PSD then is equation (4) divided by equation (5). As this final step involves dividing the PSD by the $PSD_{max}$, optionally the term $[1/\Sigma I_{if}]$ can be omitted from equations (4) and (5), since it cancels.

As noted earlier, two further optional refinements can also be applied during the calculation. Firstly, if the measured mass spectrum does not contain a mass peak within the largest expected mass error of the peak in the theoretical isotopic mass spectrum, or, a peak does exist, but has an intensity difference greater in magnitude than the largest expected intensity error, a penalty is applied. Secondly, if the theoretical isotopic mass spectrum peak is of low intensity compared to the baseline noise of the measured mass spectrum, that theoretical peak is excluded from the comparison process. It has been found that these two refinements significantly contribute to two advantages of the method: its high selectivity and high accuracy.

For the first case, a peak is defined as "missing" if the spectral distance of the individual peak, SD, is greater than or equal to 1.0. Two approaches are then used to generate mass and intensity errors to be used in the calculation of the PSD: manual and automatic. In the manual approach, a penalty factor is effectively set by the user, as will be described below. In the automatic approach, a penalty factor is calculated based on the signal to noise ratio, S/N, the peak would be expected to have, had it existed in the measured spectrum. The S/N is calculated as:

$$S/N = B \cdot (I_{ip}/100)/I_{noise} \qquad \text{equation (6)}$$

where B is the intensity of the monoisotopic mass peak in the measured spectrum to which the candidate theoretical isotopic spectrum is to be compared, and the measured noise value of this peak is $I_{noise}$. In other words, the peak, had it existed, would be expected to have an intensity of $I_{ip}/100$, $I_{ip}$ being expressed in %, and this calculation scales this to the intensity scale of the measured spectrum, before dividing it by the noise. An error value dE is then assigned depending on the S/N: If S/N<3, dE=1.0 is assigned; if 3<=(S/N)<9, dE=2.0 is assigned; if 9<=S/N, dE=4.0 is assigned. Of course various different error values could be assigned, including a continuously variable range. The automatic penalty to account for the "missing" peaks significantly improves the selectivity of the method.

In the manual approach, three settings have been implemented: low, medium and high. For the low setting, dE=1.0 is assigned. For the medium setting, dE=2.0 is assigned. For the high setting, dE=4.0 is assigned. Of course other settings could be used.

In both manual and automatic approaches, the error value dE is applied depending on whether the peak is "missing" because:
(i) $dM_{ip} > M_{exp}$ or
(ii) $dI_{ip} > I_{exp}$ or
(iii) both $dM_{ip} > M_{exp}$ and $dI_{ip} > I_{exp}$.

In the calculation of SD, the following occurs in each case:
(i) the term $dM_{ip}/M_{exp}$ only is replaced with dE
(ii) the term $dI_{ip}/I_{exp}$ only is replaced with dE
(iii) both the term $dM_{ip}/M_{exp}$ and $dI_{ip}/I_{exp}$ are replaced with dE.

In the second further preferred refinement, where the theoretical isotopic mass spectrum peak is of low intensity compared to the baseline noise of the measured mass spectrum, a form of thresholding is applied. This refinement prevents the former missing peak refinement from being activated for very small peaks that are expected to be buried in the noise of the measured spectrum. Again, manual and automatic approaches may be implemented. In the manual approach the user defines a threshold in the range 0 to 100%. In the automatic approach, the threshold, in this case, is set to 4 times the noise value, in %. It will be understood that other threshold values could be chosen. If, again, B is the intensity of the monoisotopic mass peak in the measured spectrum to which the candidate theoretical spectrum is to be compared, and the measured noise value of this peak is $I_{noise}$, then the threshold is set to $100 \cdot (4 \cdot I_{noise}/B)$. The threshold thus calculated is then used to select the theoretical isotope mass peaks used in the calculation of the pattern spectral distance. If the theoretical peak has an intensity lower than the threshold, it is deselected and not used in the calculation, (where the highest peak of the isotope pattern has an intensity of 100%).

The threshold thus applied has been found to significantly increase the selectivity of the method. Again, other threshold settings could be used.

Still a further optional refinement to the method relates to the normalization process described above where the measured mass spectrum intensity (or the theoretical isotopic peak intensity) is scaled or normalized to make the peak height of the mass peak substantially equal to the peak height of the candidate composition matched to it. This scaling or normalization enables the peaks of the measured mass spectrum to be matched to those of the theoretical isotopic spectrum. This is desirable as the calculation of SD involves dI, the difference in intensity between the measured and theoretical peaks, and the peaks are thus preferably on the same absolute scale for this to be meaningful. This is step 130 of FIG. 2. The further optional refinement is for a further normalization or scaling process to be applied subsequently, immediately prior to the calculation of the pattern spectral distance, PSD, having found the peaks in the measured mass spectrum that best correspond to the selected peaks in the theoretical isotopic mass spectrum. This optional step is applied between steps 140 and 150 of FIG. 2. This applies a normalization or a scaling factor either to the theoretical spectral intensities or to the measured mass spectrum so as to minimise the differences $dI_{ip}$ of all the peaks in the pattern. As with the earlier scaling or normalization, it does not matter whether the intensity of the theoretical isotopic spectrum is adjusted, or that of the measured mass spectrum, so long as the result is to minimise the differences of intensity of all peaks. In the preferred embodiment, it is the theoretical isotopic spectrum that is adjusted.

Two further types of this scaling or normalization are described here, though others are possible: linear fit and quadratic fit. For both, a normalization or scaling factor, N, is calculated. For the linear fit, the normalization or scaling factor is calculated such that the sum of the intensity deviations between all the selected peaks in the theoretical pattern and the corresponding peaks in the measured pattern is minimized. Then, the normalization factor is calculated as $$N = \Sigma I_{(measured,abs)} / \Sigma I_{(theory,abs)} \qquad \text{equation (7)}$$

where $I_{(measured,abs)}$ is the absolute intensity of the measured peak, and $I_{(theory,abs)}$ is the absolute intensity of the theoretical peak and the summation is over all the selected peaks in the theoretical isotopic mass spectrum. For the quadratic fit, the normalization factor is calculated such that the sum of the squared intensity deviations between all the selected peaks in the theoretical pattern and the corresponding peaks in the measured pattern is minimized. Then, the normalization factor is calculated as $$N = \Sigma (I_{(measured,abs)} \cdot I_{(theory,abs)}) / \Sigma (I_{(theory,abs)} \cdot I_{(theory,abs)}) \qquad \text{equation (8)}.$$

Again, the summation is over all the selected peaks in the theoretical isotopic mass spectrum. The factor N is then applied to the theoretical intensities to produce revised theoretical isotopic mass peak intensities:

$$I_r = N \cdot I_{theory} \qquad \text{equation (9)}.$$

These revised intensities are then used as described above in the calculation of the pattern spectral distance. Of course whilst this additional normalization has here been applied to the theoretical peak intensities, it could equally be applied to the measured peak intensities instead.

Optionally, as noted earlier, the PSD for each candidate is converted to a pattern spectral fit, PSF, which ranges from 0 to 100%, where the PSF is the larger of 0.0 and 100·(1.0−PSD).

In the method, the user supplies a list of peaks from the measured spectrum specifying the position and intensity of each, and identifies the peak of interest for which a composition is required. The method then involves finding the peaks that best match the isotopic spectra of candidate compositions, as already described. Peaks in the measured spectrum that are not related to the peak of interest, i.e. that are not isotopic variants of the peak of interest, are considered along with those that are related, as the user makes no assumptions about which peaks are relevant. Unrelated peaks will either produce a large value of SD because they are in the wrong position or have the wrong intensity to match an isotopic peak of a candidate, or both, or will produce a large PSD because they are unrelated to the peak of interest and the pattern of peaks is a poor match to the isotopic pattern of the candidate. It is this that makes the method effective at removing the requirement for an experienced spectroscopist to review the mass spectrometry data.

Throughout the foregoing description, embodiments of the invention have been described in relation to mass spectra. However, the invention also functions with spectra that are measured in other domains, such as, e.g., frequency or time, where those domains are related to mass. The measured and the theoretical spectra are preferably in the same domain. However, the measured and the theoretical spectra may be in different domains, provided each domain is related to mass, since the spectra may still be computationally compared. In the case of frequency, such spectra are related to mass spectra when they are derived from mass spectrometers which measure image current oscillation frequencies, such as, for example, FT-ICR spectrometers, some types of electrostatic trap and the Orbitrap™. In the case of time, such spectra are related to mass spectra when they are derived from spectrometers such as in time-of-flight and some other types of electrostatic trap mass analysers. All the equations above which recite quantities of mass, may have quantities of frequency or time substituted in order to use the method embodying the present invention with those corresponding types of spectra. Accordingly, it will be understood that, although some preferred embodiments will determine the mass (or even the mass to charge ratio m/z) of the ions, this is not essential to the successful operation of the invention. Many different physical parameters such as (but not limited to) time of flight, frequency, voltage, magnetic field, angular deflection etc. or a combination of these, might be measured (dependent for example on the chosen method of ion detection or method of ion separation), each of which is related to or allows derivation of the ion mass or m/z. However it is not necessary that the mass itself is calculated in each case before the method of the present invention can be applied; it may be computationally more efficient not to convert measured parameters in a non-mass space into mass. Indeed, it may be computationally desirable to generate, for example, the theoretical isotopic peaks in an arbitrary set of units and to normalize or scale these to the measured mass (or vice versa) by way of a scaling factor applied during calculation of SD, PSD etc. Where a parameter related to mass but not mass itself is employed, and when, in the method, the combined 'mass' of a candidate elemental composition is found to equal the measured 'mass' within a certain tolerance, for example, the combination of the quantities might not be by simple addition, it might instead be by addition of the square of the quantity, for example, as appropriate when combining terms representative of mass that are not converted to mass space. Thus the term "a quantity indicative of mass" is to be interpreted broadly to encompass mass and other quantities. Specifically, in the claims and description, "mass" can mean physical mass or any quantity indicative of physical mass. Likewise, where a 'position' of a measured peak or theoretical isotopic peak is referred to, this represents any value related to mass—that is, any value typically displayed in the horizontal (x) direction in a spectrum, as opposed to intensity in the vertical direction.

The method embodying the present invention and as described above was applied to the example mass spectrum shown in FIG. 1. The following parameters were used:

Mass tolerance=5.00 ppm
Expected mass error=3.00 ppm
Expected intensity error=3.00%

The options to abundance weight both mass and intensity errors were used. The threshold option was set to automatic, the missing peak penalty was set to automatic, and the type of normalization used was quadratic. Table 2 shows the results ordered by best pattern spectral fit.

TABLE 2

Candidates for the monoisotopic mass 386.2545 Daltons found by the method of the present invention.

| Compound | Mass deviation [ppm] | Pattern Spectral Fit [%] |
| --- | --- | --- |
| C21•H32•O2•N5. | −1.43 | 65.88 |
| C9•H28•O1•N14•F2. | 3.08 | 0.00 |
| C19•H38•N4•[32]S2. | 3.26 | 0.00 |
| C14•H32•N11•[32]S1. | −3.20 | 0.00 |
| C14•H29•O1•N11•F1. | 2.57 | 0.00 |
| C23•H34•O3•N2. | −4.91 | 0.00 |
| C18•H35•O1•N6•[35]Cl1. | −2.69 | 0.00 |
| C15•H38•N7•[35]Cl2. | −3.95 | 0.00 |
| C15•H37•O4•N5•[35]Cl1. | 4.25 | 0.00 |
| C18•H33•O3•N5•F1. | −4.39 | 0.00 |
| C16•H35•N5•F3•[32]S1. | −3.83 | 0.00 |
| C20•H38•O1•[35]Cl1•F3. | −3.31 | 0.00 |
| C11•H34•O3•N10•[32]S1. | 3.74 | 0.00 |
| C14•H37•N7•F1•[32]S2. | 3.78 | 0.00 |
| C13•H34•O1•N9•[35]Cl1•F1. | −2.17 | 0.00 |
| C18•H36•N3•[35]Cl1•F3. | 0.16 | 0.00 |
| C16•H33•N9•[35]Cl1. | 0.79 | 0.00 |
| C4•H26•O2•N20. | 0.75 | 0.00 |
| C17•H37•O7•N1•F1. | −0.93 | 0.00 |
| C16•H31•O2•N8•F1. | −0.91 | 0.00 |
| C21•H33•O1•N2•F3. | 1.42 | 0.00 |
| C20•H36•O6•N1. | 2.03 | 0.00 |
| C21•H40•O1•N1•[32]S2. | −0.21 | 0.00 |
| C19•H30•O1•N8. | 2.05 | 0.00 |
| C11•H30•O2•N11•F2. | −0.39 | 0.00 |
| C15•H35•O6•N4•F1. | 2.55 | 0.00 |
| C13•H36•O4•N7•[32]S1. | 0.26 | 0.00 |
| C9•H31•N14•F1•[32]S1. | −2.69 | 0.00 |
| C18•H38•O3•N1•F2•[32]S1. | 2.60 | 0.00 |
| C11•H32•N12•[35]Cl1•F1. | 1.30 | 0.00 |
| C21•H36•N2•F2•[32]S1. | −4.34 | 0.00 |
| C13•H32•O3•N8•F2. | −3.87 | 0.00 |
| C23•H37•[35]Cl1•F2. | −0.35 | 0.00 |
| C6•H28•O3•N17. | −2.73 | 0.00 |
| C19•H31•N5•F3. | 4.90 | 0.00 |
| C24•H32•N2•F2. | 4.38 | 0.00 |

There is only one candidate with a non-zero PSF. This candidate is the MH+ form of Buspirone, the compound used in the sample. Note that in Table 1, the results from the prior art elemental composition calculation, this compound is listed at number 12, and there is nothing to suggest to the untrained eye from the data in Table 1 that this should be the correct compound. This illustrates the remarkable selectivity and accuracy of the method of the present invention.

As noted earlier, the number of elemental composition candidates grows rapidly for compounds of higher mass. The lower the mass and intensity errors of the measured mass spectrum are, the higher in mass the spectral distance method will work and correctly assign the compound. With the Orbitrap™ mass analyser, at present, typically a mass precision of 2 ppm and intensity precision of 3% is possible. With the prior art elemental composition calculation, even with these tight tolerances, above mass 300 the number of candidates becomes so large that the mass deviation of the monoisotopic peak cannot solely be used to determine reliably the most likely composition candidate, as was illustrated for mass 386 Daltons above. To test the method of the present invention at higher mass, with typical Orbitrap™ mass and intensity precisions, a spectrum of the peptide C105 H169 O25 N27 (ALELFRALELFRALELFR) was created, the monoisotopic mass of the MH+ ion being 2207.26987.

The prior art elemental composition calculator produced 241 candidates. Using the method of the present invention, the pattern spectral fit, PSF, was calculated. The threshold was set to 1%, the missing peak penalty set to high and base peak normalization was used. The nine top ranking composition candidates produced are shown in Table 3. The candidate with the largest PSF is the correct candidate. This illustrates the remarkably high selectivity and high accuracy of the method.

TABLE 3

| Elemental composition candidate | Mass deviation [ppm] | PSF [%] |
|---|---|---|
| C105•H168•O25•N27. | −0.02 | 99.30 |
| C106•H164•O21•N31. | −0.63 | 72.33 |
| C104•H172•O29•N23. | 0.59 | 72.27 |
| C102•H160•O19•N37. | 0.59 | 71.53 |
| C99•H164•O19•N37•[32]S1. | −0.94 | 58.78 |
| C101•H164•O23•N33. | 1.20 | 48.17 |
| C109•H172•O27•N21. | −1.24 | 47.62 |
| C110•H168•O23•N25. | −1.84 | 22.07 |
| C100•H168•O27•N29. | 1.80 | 21.32 |

To further describe the method, a worked example will now be given. For simplicity, a synthetic mass spectrum has been created, for the MH+ molecule of Buspirone, mass 386.255052, C21H32O2N5, along with several intense background peaks. The mass peaks of the MH+ molecule of Buspirone have small offsets applied to both mass and intensity to "distort" the spectrum so as to represent the inaccuracy and imprecision of a mass spectrometer.

TABLE 4

| Theoretical peaks | | | Distorted peaks | | | Mass Difference | | Intensity Difference | |
|---|---|---|---|---|---|---|---|---|---|
| Mass | Intensity | Intensity Relative | Mass | Intensity | Intensity Relative | [ppm] | mmu | Absolute [%] | Relative [%] |
| 386.255052 | 91110.40 | 100.00 | 386.25450 | 5170118.45 | 100.000 | −1.42 | −0.55 | 0.00 | 0.00 |
| 387.258085 | 22347.20 | 24.53 | 387.25850 | 1243578.68 | 24.053 | 1.32 | 0.51 | −0.48 | −1.92 |
| 388.260860 | 2996.30 | 3.29 | 388.25970 | 166738.30 | 3.2250 | −2.60 | −1.01 | −0.07 | −1.91 |
| 389.263471 | 288.04 | 0.32 | 389.26431 | 16028.90 | 0.3100 | 2.57 | 1.00 | 0.00 | −1.20 |

TABLE 5

| Mass | Intensity | Intensity Relative |
|---|---|---|
| 386.2440 | 3000000.0 | 58.03 |
| 387.2555 | 4900000.0 | 94.78 |
| 388.2590 | 172928.4 | 3.34 |
| 389.2620 | 172928.4 | 3.34 |

TABLE 6

| Mass | Intensity | Intensity Relative |
|---|---|---|
| 386.24400 | 3000000.00 | 58.0257 |
| 386.25450 | 5170118.45 | 100.0000 |
| 387.25550 | 4900000.00 | 94.7754 |
| 387.25850 | 1243578.68 | 24.053 |
| 388.25900 | 172928.40 | 3.3448 |
| 388.25970 | 166738.30 | 3.2250 |
| 389.26200 | 172928.40 | 3.3448 |
| 389.26431 | 16028.90 | 0.3100 |

TABLE 7

| Name | Value | Comment |
|---|---|---|
| Charge | 1 | The charge state of the pattern |
| Keep Best | 10 | This number of candidates is investigated further, having the smallest deviation between theoretical and measured mass |
| Mass Tolerance | 10 ppm | Monoisotopic mass of candidates must lie in this window |
| Electron Rule | Not used | Determines whether candidates have eve/odd number of electrons |
| RDB Limit | −1 . . . 20 | The allowed RDB range |
| C atoms | 0 . . . 200 | Number of C atoms that a candidate may have |
| H atoms | 0 . . . 400 | Number of H atoms that a candidate may have |
| N atoms | 0 . . . 20 | Number of N atoms that a candidate may have |
| O atoms | 0 . . . 20 | Number of O atoms that a candidate may have |
| S atoms | 0 . . . 5 | Number of S atoms that a candidate may have |
| Cl atoms | 0 . . . 4 | Number of Cl atoms that a candidate may have |

TABLE 8

| Mass | Mass deviation [ppm] | Composition |
|---|---|---|
| 386.2546 | −0.21 | C21H40ONS2 |
| 386.2544 | 0.26 | C13H36O4N7S |
| 386.2542 | 0.75 | C4H26O2N20 |
| 386.2542 | 0.77 | C17H39O5N2Cl |

TABLE 8-continued

| Mass | Mass deviation [ppm] | Composition |
|---|---|---|
| 386.2542 | 0.79 | C16H33N9Cl |
| 386.2551 | −1.43 | C21H32O2N5 |
| 386.2537 | 2.03 | C20H36O6N |

TABLE 8-continued

| Mass | Mass deviation [ppm] | Composition |
|---|---|---|
| 386.2537 | 2.05 | C19H30ON8 |
| 386.2555 | −2.69 | C18H35ON6Cl |
| 386.2556 | −2.73 | C6H28O3N17 |

TABLE 9

|  | Mass | Intensity | Intensity Relative |
|---|---|---|---|
| A0 | 386.255052 | 91110.40 | 100.00 |
| A1 | 387.258085 | 22347.20 | 24.53 |
| A2 | 388.260860 | 2996.30 | 3.29 |
| A3 | 389.263471 | 288.04 | 0.32 |

TABLE 10

| | | Measured Mass | | | | | | |
|---|---|---|---|---|---|---|---|---|
| Theoretical Mass | Intensity Relative | 386.24400 58.0257 | 386.25450 100.0000 | 387.25550 94.7754 | 387.25850 24.0532 | 388.25900 3.3448 | 388.25970 3.2250 | 389.26200 3.3448 | 389.26431 0.3100 |
| 386.25505 | 100.00 | 16.933 | 0.476 | 863.376 | 866.333 | 1729.683 | 1730.287 | 2595.159 | 2597.165 |
| 387.25808 | 24.53 | 872.947 | 864.204 | 23.521 | 0.391 | 861.569 | 862.172 | 1724.889 | 1726.882 |
| 388.26086 | 3.29 | 1731.629 | 1722.820 | 863.669 | 860.583 | 1.597 | 0.996 | 859.508 | 861.492 |
| 389.26347 | 0.32 | 2585.699 | 2576.850 | 1719.750 | 1716.911 | 860.147 | 859.548 | 1.614 | 0.718 |

Spectral Distance (SD) between the Theoretical Mass and the Measured Mass

TABLE 11

Relative intensities of the peaks after quadratic normalization.

| Theoretical Mass | Intensity Relative | Intensity Relative after quadratic normalization |
|---|---|---|
| 386.255052 | 100.00 | 99.89 |
| 387.258085 | 24.53 | 24.50 |
| 388.260860 | 3.29 | 3.28 |
| 389.263471 | 0.32 | 0.32 |

TABLE 12

| | $dM/M_{exp}$ | $dI/I_{exp}$ | $(dM/M_{exp})^2$ | $(dI/I_{exp})^2$ | $((dM/M_{exp})^2) * I_f$ | $((dI/I_{eep})^2) * I_f$ | $I_f$ |
|---|---|---|---|---|---|---|---|
| | | | Calculation of PSD: | | | | |
| A0 | −0.4762 | −0.0372 | 0.226730 | 0.001385 | 0.226477 | 0.001383 | 0.9989 |
| A1 | 0.3575 | 0.1490 | 0.127790 | 0.022204 | 0.031309 | 0.005440 | 0.2450 |
| A2 | −0.9957 | 0.0200 | 0.991471 | 0.000399 | 0.032570 | 0.000013 | 0.0328 |
| A3 | 0.7185 | 0.0019 | 0.516194 | 0.000004 | 0.001630 | 0.000000 | 0.0032 |
| | | | sum: | | 0.291986 | 0.006836 | 1.2799 |
| | | SQRT(sum(((dM/M_{exp})^2) * I_f) + sum(((dI/I_{exp})^2) * I_f)) | | | | 0.54664 | |
| | | | $1/sum(I_f)$ | | | 0.7813 | |
| | | | abundance weighted PSD | | | 0.4271 | |
| | | | Calculation of $PSD_{max}$: | | | | |
| A0 | 1 | 1 | 1 | 1 | 0.998884 | 0.998884 | 0.9989 |
| A1 | 1 | 1 | 1 | 1 | 0.245002 | 0.245002 | 0.2450 |
| A2 | 1 | 1 | 1 | 1 | 0.032850 | 0.032850 | 0.0328 |
| A3 | 1 | 1 | 1 | 1 | 0.003158 | 0.003158 | 0.0032 |
| | | | sum: | | 1.279894 | 1.279894 | 1.2799 |
| | | SQRT(sum(((dM/M_{exp})^2) * I_f) + sum(((dI/I_{exp})^2) * I_f)) | | | | 1.5999 | |
| | | | $1/sum(I_f)$ | | | 0.7813 | |
| | | | abundance weighted $PSD_{max}$ | | | 1.2500 | |
| | | | Calculation of normalized PSD: | | | | |
| | | abundance weighted PSD/abundance weighted $PSD_{max}$ | | | | 0.3417 | |

TABLE 13

PSD results for all the candidates of Table 8.

| Elemental composition candidate | Mass deviation [ppm] | PSD |
|---|---|---|
| C21•H32•O2•N5. | −1.428 | 0.342 |
| C14•H32•N11•[32]S1. | −3.203 | 1.000* |
| C18•H35•O1•N6•[35]Cl1. | −2.69 | 1.000* |
| C16•H33•N9•[35]Cl1. | 0.786 | 1.000* |
| C4•H26•O2•N20. | 0.747 | 1.000* |
| C20•H36•O6•N1. | 2.034 | 1.278 |
| C21•H40•O1•N1•[32]S2. | −0.214 | 1.279 |
| C19•H30•O1•N8. | 2.048 | 1.290 |
| C13•H36•O4•N7•[32]S1. | 0.259 | 1.751 |
| C6•H28•O3•N17. | −2.729 | 3.023 |

*No mass peaks were found within expected mass and expected intensity errors for all the peaks in the isotope pattern, so the missing peak penalty was applied for each missing peak and the PSD becomes 1.0.

The list of peaks is given in Table 4. The background peaks are listed in Table 5. Their relative intensities are normalized to the distorted MH+ Buspirone peaks. Note the intense peaks close to the first two peaks in Table 4. A method embodying the present invention is then applied to a combination of data from both Tables 4 and 5 as summarized in Table 6.

In Table 7 the parameters for the prior art elemental candidate composition calculation are given. This calculation produced the candidates shown in Table 8. The correct composition is shown in bold, at sixth place in the table.

As previously described, the method embodying the present invention now involves generating a theoretical isotopic mass spectrum for each of the candidate compositions. An example for the correct composition C21H32O2N5 is given in Table 9. Using the scaled intensity of the measured mass spectrum, the next step is to find, for each selected theoretical isotopic mass peak, the scaled measured mass peak closest in spectral distance, using equation (1). Table 10 shows the spectral distances between the measured peaks and the theoretical peaks for the candidate of Table 9, with the closest highlighted in bold.

For this example, the expected mass error is set to 3.0 ppm, the expected intensity error to 3% and the noise value to 7500 (absolute intensity). The intensity threshold is set to automatic. This threshold relates to the second further refinement described earlier, where the theoretical isotopic mass spectrum peak is of low intensity compared to the baseline noise of the measured mass spectrum. Then, a form of thresholding is applied and only peaks in the theoretical isotopic mass spectrum above the threshold are selected for further processing, as peaks smaller than this in the measured spectrum will likely be hidden by noise. The missing peak penalty, as described earlier, is also set to the automatic option.

Once the closest peaks have been found, an optional step of normalization of intensity can be performed, as described earlier, to best match the average intensities of the found measured peak set and the theoretical isotopic mass spectrum. In this example the quadratic normalization option is used, as in equation (8). This changes the relative intensities of the peaks as shown in Table 11.

In this example, the pattern spectral distance, PSD, is abundance weighted, as in equation (4). It is also normalized for the number of peaks in the pattern using the abundance weighted $PSD_{max}$ of equation (5). The terms used in these calculations are given in Table 12 for the candidate of Table 9. As shown in Table 12 the final abundance weighted PSD normalized by the abundance weighted $PSD_{max}$ is 0.3417 for the candidate. Table 13 shows the results of the same calculations for the other nine candidates of Table 8. It can be seen that the correct compound has been identified as the most likely candidate composition enabling the sample, in a real case, to be characterized.

The method may be implemented in a number of ways. Most conveniently, the invention is implemented as computer software. This may be executed either locally to a mass spectrometer, taking mass spectral (or other, related) data in real time and/or using historic data and analysing it to identify a most likely elemental composition for measured peaks of interest. Such identification can be cross checked by MS/MS or $MS^n$ experiments subsequently. Alternatively, the software can be executed at a remote location, based upon historic experimental data loaded into a memory, for example, and analysed in accordance with the methods described above.

Nevertheless it is possible for embodiments of the invention to be implemented in firmware within a mass spectrometer instead, for example. Other modifications and alternatives will be apparent to the skilled person.

The invention claimed is:

1. A computer implemented method of characterizing a sample by identifying a most likely elemental composition of a measured peak of interest in a spectrum obtained from that sample, comprising the steps of:
   (a) identifying, for the peak of interest in the spectrum of the sample, a plurality of elemental compositions having a peak whose position lies within a predetermined tolerance of the position of the said measured peak of interest;
   (b) forming a set of candidate compositions from the identified plurality of elemental compositions;
   (c) generating a theoretical isotopic spectrum for each of the candidate compositions in the said formed set thereof;
   (d) selecting peaks within each theoretical isotopic spectrum thus generated, for further processing;
   (e) for each candidate composition of the set, in turn:
      (i) scaling the intensity of at least one of: all the selected peaks of the theoretical isotopic spectrum of the particular candidate composition under consideration, and/or all the peaks of the measured spectrum, to reduce the difference between the intensities of the peak of interest and the corresponding peak of the candidate composition;
      (ii) calculating a spectral distance, SD, between peaks in the theoretical isotopic spectrum and peaks in the measured spectrum based upon both the difference dM in the relative positions of a given peak in the theoretical isotopic spectrum and a given peak in the measured spectrum, and also the relative differences dI in scaled intensity thereof, wherein SD increases monotonically with dM and dI;
      (iii) either:
         for the peaks in the theoretical isotopic spectrum selected in step (d), identifying the peak in the measured spectrum which is considered most closely to correspond with a particular one of the peaks in the theoretical isotopic spectrum by determining the measured peak that has the lowest SD; or
         for the peaks in the measured spectrum, identifying the peak in the theoretical isotopic spectrum selected in step (d) which is considered most closely to correspond with a particular one of the peaks in the measured spectrum by determining the theoretical isotopic peak that has the lowest SD;
      (iv) calculating a pattern spectral distance (PSD) for a particular candidate composition, based upon a combination of both dM and dI between the measured peaks and the theoretical isotopic peaks, where the measured or theoretical isotopic peaks are those which have been identified in step (e) (iii), and wherein PSD increases monotonically with dM and dI;

(v) normalizing the PSD for n, the number of selected peaks in the theoretical isotopic spectrum;

(f) identifying which of the set of candidate elemental compositions of the measured peak of interest is the most likely elemental composition thereof, by determining which candidate composition has the lowest PSD; and (g) outputting data representative of the identified most likely elemental composition of the measured peak of interest;

wherein steps (a)-(g) are performed by a computer executing computer software;

wherein the measured spectrum is a mass spectrum generated by analyzing the sample in a mass spectrometer;

wherein the PSD is weighted according to the abundance of the peaks in either the theoretical isotopic mass spectrum or the measured mass spectrum such that a mass and/or intensity error of a less intense peak affects the PSD less than the same mass or intensity error of a more intense peak; and wherein the weighted PSD is calculated according to one of:

$$PSD = \sqrt{[((dM_1/M_{exp})^2 * I_{1f}) + ((dM_2/M_{exp})^2 * I_{2f}) + \ldots + ((dI_1/I_{exp})^2 * I_{1f}) + ((dI_2/I_{exp})^2 * I_{2f}) + \ldots]} \quad (A)$$

$$PSD = \sqrt{[((dM_1/M_{exp}) + ((dM_2/M_{exp}) + \ldots + ((dI_1/I_{exp})^2 * I_{1f}) + ((dI_2/I_{exp})^2 * I_{2f}) + \ldots]} \quad (B)$$

$$PSD = \sqrt{[((dM_1/M_{exp})^2 * I_{1f}) + ((dM_2/M_{exp})^2 * I_{2f}) + \ldots + ((dI_1/I_{exp})^2) + ((dI_2/I_{exp})^2) + \ldots]} \quad (C)$$

and where:

the intensity of the selected theoretical isotopic mass peak is $I_{ip}$; and $I_{1f}$, $I_{2f}$ etc. are fractional intensities.

2. A method according to claim 1, wherein:
SD is defined as any of:

$$SD = \sqrt{((dM/M_{exp})^2 + (dI/I_{exp})^2)} \quad (a)$$

$$SD = |dM/M_{exp}| + |dI/I_{exp}| \quad (b)$$

$$SD = \sqrt{((dM/M_{exp})^2) + dI/I_{exp}|} \quad (c)$$

$$SD = |dM/M_{exp}| + \sqrt{((dI/I_{exp})^2)} \quad (d)$$

and wherein
$M_{exp}$ = expected positional error,
$I_{exp}$ = expected intensity error.

3. A method according to claim 1 wherein a criterion for selecting a theoretical isotopic peak comprises applying a threshold, such that only peaks of the theoretical isotopic spectrum having intensities greater than the threshold are selected for further processing.

4. A method according to claim 3, wherein the threshold is mathematically related to the noise in the measured spectrum.

5. A method according to claim 4, wherein the threshold in percent is set to $100 \cdot (4 \cdot I_{noise}/B)$, where B is the intensity of the identified peak of interest and the measured noise value of this peak is $I_{noise}$.

6. A method according to claim 1 wherein between steps (e)(iii) and (e)(iv) the selected theoretical isotopic peaks and/or the peaks of the measured spectrum are scaled in intensity so as to minimize the sum of the difference in intensities, dI, between the intensity of each selected theoretical isotopic peak and the intensity of the corresponding measured peak.

7. A method according to claim 6 wherein the scaling is performed using a scaling factor N which is calculated and applied according to $$I_r = N \cdot I_1$$

where:
$I_r$ is a scaled peak intensity, and
$I_1$ is the intensity of the peak in the spectrum to be scaled, either the selected theoretical isotopic peak intensity or the measured peak intensity;

and where:
$I_{(1,abs)}$ is the absolute intensity of the peak in the spectrum to be scaled,
$I_{(2,abs)}$ is the absolute intensity of the corresponding peak in the other spectrum which is not to be scaled, and all summations are over all the peaks in the spectrum to be scaled;

and in which the scaling factor is calculated as one of $$N = \Sigma I_{(2,abs)} / \Sigma I_{(1,abs)} \quad (a)$$

$$N = \Sigma (I_{(2,abs)} \cdot I_{(1,abs)}) / \Sigma I_{(1,abs)} \cdot I_{(1,abs)}). \quad (b)$$

8. A method according to claim 1 wherein the step of normalizing the PSD for n comprises multiplying the PSD by $1/\sqrt{(2*n)}$.

9. A method according to claim 1, wherein the step of normalizing the PSD for n, the number of peaks in the theoretical isotopic spectrum, comprises multiplying the PSD by $$1/\sqrt{[2*I_{1f} + 2*I_{2f} + \ldots]} \quad (a)$$

$$1/\sqrt{[n + I_{1f} + I_{2f} + \ldots]} \quad (b)$$

$$1/\sqrt{[n + I_{1f} + I_{2f} + \ldots]} \quad (c)$$

for the cases (A), (B) and (C) of claim 1, respectively.

10. A method according to claim 1 wherein a peak is defined as missing if SD is larger than or equal to a given threshold, and that the calculation of the PSD involves applying a penalty for such missing peaks, the penalty further increasing the value of PSD.

11. A method according to claim 10 wherein the threshold is 1.0.

12. A method according to claim 10, wherein the penalty applied is calculated based on the signal to noise ratio, S/N, the peak would be expected to have, had it existed in the measured spectrum.

13. A method according to claim 10 wherein the penalty is dE, and dE is applied in one of the following ways:

(a) if $dM_{ip} > M_{exp}$ the term $dM_{ip}/M_{exp}$ is replaced with dE
(b) if $dI_{ip} > I_{exp}$ the term $dI_{ip}/I_{exp}$ is replaced with dE
(c) if both $dM_{ip} > M_{exp}$ and $dI_{ip} > I_{exp}$ both the term $dM_{ip}/M_{exp}$ and $dI_{ip}/I_{exp}$ are replaced with dE,
and where dE is greater than or equal to 1.0.

* * * * *